US005942510A

United States Patent [19]

Floyd et al.

[11] Patent Number: 5,942,510

[45] Date of Patent: Aug. 24, 1999

[54] PHARMACEUTICAL COMPOSITION CONTAINING LAMOTRIGINE

[75] Inventors: Alison Green Floyd, Raleigh; Sunil Jain, Cary, both of N.C.

[73] Assignee: Glaxo Wellcome Inc., Research Triangle Park, N.C.

[21] Appl. No.: 08/973,798

[22] PCT Filed: Jun. 20, 1996

[86] PCT No.: PCT/EP96/02759

§ 371 Date: Dec. 9, 1997

§ 102(e) Date: Dec. 9, 1997

[87] PCT Pub. No.: WO97/00681

PCT Pub. Date: Jan. 9, 1997

[30] Foreign Application Priority Data

Jun. 23, 1995 [GB] United Kingdom .................. 9512854

[51] Int. Cl.[6] .................................................. A61K 31/53

[52] U.S. Cl. .......................................................... 514/242

[58] Field of Search ............................................ 514/242

[56] References Cited

U.S. PATENT DOCUMENTS

| | | | |
|---|---|---|---|
| 4,406,888 | 9/1983 | Aguiar et al. | 424/175 |
| 4,486,354 | 12/1984 | Baxter et al. | 260/465 |
| 4,602,017 | 7/1986 | Sawyer et al. | 514/242 |
| 4,847,249 | 7/1989 | Sawyer et al. | 514/242 |
| 5,059,619 | 10/1991 | Haeger et al. | 514/410 |
| 5,283,067 | 2/1994 | Geller et al. | 424/489 |
| 5,545,637 | 8/1996 | Fu et al. | 514/233.5 |
| 5,629,312 | 5/1997 | Bousseau et al. | 514/242 |

FOREIGN PATENT DOCUMENTS

| | | |
|---|---|---|
| A0 247 892 | 12/1987 | European Pat. Off. . |
| 2702 149 | 9/1994 | France . |
| 94 13296 | 6/1994 | WIPO . |
| A95 05179 | 2/1995 | WIPO . |
| 96 17611 | 6/1996 | WIPO . |
| 96 20935 | 7/1996 | WIPO . |
| 97 00681 | 1/1997 | WIPO . |

OTHER PUBLICATIONS

Schmitt et al J. Pharm. Sci. 85(11):1215–1219 "Moisture–Dependent Crystallization of Amorphous Lamotrigine Mesylate", 1996.

*Primary Examiner*—Shep K. Rose
*Attorney, Agent, or Firm*—Shah R. Makujina

[57] ABSTRACT

A lyophilized formulation of lamotrigine having been prepared by lyophilizing a frozen sterile aqueous solution of lmotrigine mesylate in which the pH is from 2.4 to 4.

27 Claims, No Drawings

PHARMACEUTICAL COMPOSITION CONTAINING LAMOTRIGINE

This application is filed pursuant to 35 U.S.C.§ 371 as a United States National Phase Application of International Application No. PCT/US96/02759 filed Jun. 20, 1996 which claims priority from GB9512854.2 filed Jun. 23, 1995.

The present invention relates to a novel pharmaceutical formulation of lamotrigine, a process for its preparation, and its use in medical therapy.

Status Epilepticus (SE) is a life-threatening condition in which the high morbidity and mortality rates are directly related to the duration of seizure activity. There exists a clinical need for an antiepileptic drug (AED) that may be administered rapidly and safely via the intravenous route to achieve therapeutic plasma concentrations for the treatment of SE. The only AED currently available in an intravenous formulation is phenytoin. However, recommended doses must be administered over a period of at least 20 minutes to avoid cardiovascular side-effects (including tachycardia, bradycardia, hypotension and cardiac arrythmias) produced by the drug and its solvent, propylene glycol. Furthermore, intravenous phenytoin administration is commonly associated with injection site reactions including pain, inflammation and sclerosis.

A clinical need for an intravenous AED additionally exists for patients who are unable to swallow an oral formulation for a variety of reasons including unconsciousness (post-ictal or secondary to acute trauma), anesthesia during surgery and post-operative recovery and the presence of an intra-tracheal tube for the facilitation of mechanical ventilation.

Lamotrigine may be chemically named 3,5-diamino-6-(2,3-dichlorophenyl)-1,2,4-triazine and is disclosed in European patent 21121 and U.S. Pat. No. 4,602,017. It is useful in the treatment of SE and is commercially available under the trade name "Lamictal" as an oral tablet formulation. Typically, a therapeutic dose of lamotrigine for an adult human being comprises a loading dose of, say, 1000–1500 mg followed by a maintenance dose of, say, 500–700 mg/day. Plasma concentrations of lamotrigine of about 24 $\mu$g/mL are generally effective in controlling SE for add-on therapy, i.e. when taken concomitantly with other AEDs. Plasma concentrations of about 8–10 $\mu$g/ml are generally effective for monotherapy.

The clinical management of SE with lamotrigine would be assisted by the availability of formulations in addition to tablet formulations. In particular, as indicated above, an injectable formulation of lamotrigine would be of advantage in initiating treatment intravenously so as to obtain the required plasma concentrations and bioavailability as rapidly as possible. It would also find utility in an emergency room situation in which patients are already experiencing convulsions and are not able to take the tablet form.

The need for an injectable formulation of lamotrigine has already been recognised. Initially, its development was hampered by the poor solubility of the base form of the drug. The aqueous solubility of lamotrigine is only 0.17 mg/mL at about room temperature and does not significantly vary with pH (Table I).

TABLE 1

Solubility of Lamotrigine

| Aqueous Medium | Amount Dissolved (mg/mL) |
|---|---|
| Water at 25° C. | 0.17 |
| Water at 37° C. | 0.57 |
| HCl (pH 1.2) at 37° C. | 0.46 |
| Phosphate buffer (pH 6.0) at 37° C. | 0.68 |
| Phosphate buffer (pH 7.5) at 37° C. | 0.56 |
| 0.01N Sodium hydroxide at 25° C. | 0.30 |

Consequently, the sparingly soluble nature of lamotrigine base in water would necessitate the administration of an undesirably large volume of solution to provide a therapeutic dose. European patent 247892 and U.S. Pat. No. 4,847,249 disclose the isethionate (2-hydroxyethanesulphonate) salt of lamotrigine and its use in the provision of an injectable formulation. The isethionate salt has an aqueous solubility of 404 mg/mL at about room temperature which is substantially higher than that of the free base. It therefore enables the administration of a therapeutic dose to a patient in a much more acceptable volume of solution. However, isethionic acid is unstable if it is not prepared in situ and tends to degrade leading to uncharacterised by-products and potential regulatory complications. In situ preparation avoids this problem but is itself a cost-inefficient method for producing the isethionate salt.

Further development of an injectable formulation has been hampered by the instability of lamotrigine itself in aqueous media. In particular, lamotrigine is hydrolytically decomposed to 3-amino-5-keto-6-(2,3-dichlorophenyl)-1,2,4-triazine and 3,5-diketo-6-(2,3-dichlorophenyl)-1,2,4-triazine. Moreover, the hydrolysis is catalysed under acidic conditions. Such instability of the active ingredient is clearly undesirable for an injectable formulation for which an acceptable shelf life is a particular requirement.

An injectable formulation of lamotrigine has now been developed. The formulation is in lyophilized form and utilises the mesylate salt (that is the methanesulphonate salt) of lamotrigine. It is prepared from an aqueous solution having a pH of from 2.5 to 4. The formulation is stable in that no significant hydrolysis of the active ingredient occurs on storage. In addition, methanesulphonic acid itself is stable and, unlike isethionic acid, does not need to be prepared in situ resulting in a more efficient production process. The lyophilized formulation may also be reconstituted to provide an acceptable volume of solution containing a therapeutic dose of lamotrigine for administration to patients.

The present invention provides a lyophilized injectable formulation of lamotrigine that has been prepared by lyophilizing a substantially frozen sterile aqueous solution of lamotrigine mesylate having a pH of from 2.5 to 5, preferably 2.5 to 4.

According to a further aspect of the present invention, there is provided a lyophlized formulation containing lamotrigine mesylate present in an amount of 100 to 1000 mg, calculated as the free base.

Preferably, there is provided by the present invention, a lyophilized formulation containing lamotrigine mesylate present in an amount of 250–1000 mg, calculated as the free base, and more preferably present in an amount of substantially 250 mg, calculated as the free base.

Lamotrigine mesylate is a known salt of lamotrigine. It is disclosed in European patent 247892 and U.S. Pat. No. 4,847,249 as an intermediate in the preparation of the isethionate salt. Its aqueous solubility is 63 mg/mL at about room temperature which is significantly higher than that of the lamotrigine base. The mesylate salt is particularly amenable to the provision of a stable, lyophilised form of lamotrigine that can simply be reconstituted to obtain an injectable formulation for use in the treatment of SE.

Advantageously a lyophilized formulation according to the present invention further comprises at least one bulking agent selected from the group consisting of mannitol, dextrose, lactose, sucrose, sorbitol, and glycine, in particular mannitol. Suitably, the bulking agent is present in a lyophilized formulation according to the present invention in an amount of 192–470 mg.

There is still further provided by the present invention a process of preparing a lyophilized formulation substantially as hereinbefore described, which process comprises lyophilizing a substantially frozen sterile aqueous solution of lamotrigine mesylate in which the pH is from 2.5 to 5, preferably 2.5 to 4.

Typically, the concentration of lamotrigine, calculated as the free base, prior to lyophilization and which is employed in the preparation of a lyophilized formulation according to the present invention is preferably from 1 to 60 mg/mL, more preferably from 20 to 30 mg/mL, for example 25 mg/mL.

The mesylate salt is conveniently produced in situ by adding lamotrigine powder to an aqueous solution of methanesulphonic acid optionally containing at least one bulking agent selected from the group consisting of mannitol, dextrose, lactose, sucrose, sorbitol and glycine, preferably mannitol. Preferably, the methanesulphonic acid is present in an amount that is substantially equimolar with or greater than the amount of lamotrigine base.

The pH of the aqueous solution of lamotrigine employed in lyophilization is preferably from 2.8 to 3.5, more preferably from 3.3 to 3.5. Appropriate adjustment of the pH can be made with an aqueous solution of either methanesulphonic acid itself or sodium hydroxide.

Although one or more pharmaceutically acceptable cosolvents may be used in addition to water, it is preferred that the solution is wholly or substantially aqueous.

The aqueous solution of lamotrigine mesylate may be sterilised conventionally, for example, by filter sterilisation. It may then be dispensed into sterile, plastic or glass containers, such as ampoules or vials, in volumes of, for example, from 7 to 10 mL. The aqueous solution may be frozen at a temperature of from −10° to −24° C. The substantially frozen aqueous solution may then be maintained at this temperature until lyophilization is commenced.

Lyophilisation of the substantially frozen aqueous solution may be carried out conventionally involving, for example, both primary drying and secondary drying. Primary drying may be carried out via sublimation by using controlled application of vacuum and heat, for example under a substantial vacuum of about 0.1 to 0.5 Torr for sufficient time to effect removal of substantially all the frozen water and/or other solvent. Secondary drying is preferably carried out subsequently under a substantially similar vacuum to remove as much as possible of the last traces of adsorbed water or other solvent, thus providing a dry cake or powder.

The temperature at which primary drying is carried out ranges from −10° to 0° C. at the beginning of the process so as to maintain the solution in a substantially or completely frozen form. As the process proceeds and the product temperature reaches the desired shelf temperature, the primary drying phase is completed. The temperature at which secondary drying is carried out ranges from 25 to 35° C. in order to remove any adsorbed water and/or other solvent. The moisture content of the resulting cake or powder is preferably less than 2.5% by weight. Once the lyophilisation has been completed, the sterile, plastic or glass container containing the lyophilised formulation may then be stoppered or sealed.

The resulting lyophilized formulation is physically and chemically stable at room temperature and under accelerated storage conditions.

The lyophilised product may be reconstituted with a sterile carrier suitable for intravenous administration, such as sterile water or 5% aqueous dextrose solution and diluted as required, say, to 1 to 15 mg lamotrigine per mL with the sterile carrier. Reconstitution with water to the appropriate concentration of lamotrigine provides an isotonic solution and further dilution with 5% aqueous dextrose injection does not cause any appreciable change in the tonicity of the formulation. The reconstituted and/or diluted solution is physically and chemically stable when stored at room temperature for 24 hours, and provides an injectable formulation of lamotrigine suitable for intravenous administration.

There is therefore further provided by the present invention an injectable formulation containing lamotrigine mesylate, wherein the concentration of lamotrigine mesylate is in the range of 1 to 60 mg/ml calculated as the free base. Suitably, the formulation is prepared by reconstitution of a lyophilized formulation substantially as hereinbefore described with a sterile carrier suitable for intravenous administration.

Aptly, the lamotrigine mesylate concentration in the injectable formulation is in the range of 1 to 50 mg/ml, more aptly 1 to 20 mg/ml, such as 1 to 15 mg/ml or substantially 20 mg/ml.

The invention therefore further provides use of a lyophilized formulation substantially as hereinbefore described, in the manufacture of an injectable formulation containing lamotrigine, and still further a process of preparing an injectable formulation comprising reconstituting a lyophilized formulatoin substantially as hereinbefore described with a sterile carrier suitable for intravenous administration.

To avoid undesirable side effects, a reconstituted injectable solution of lamotrigine according to the present invention is preferably isotonic with the blood serum of the patient. An isotonic injectable solution may be obtained by including at least one bulking agent that increases the tonicity of the solution to the required level. Conveniently, the bulking agent is included in the aqueous solution prior to lyophilisation. Suitably the bulking agent is selected from the group consisting of mannitol, dextrose, lactose, sucrose, sorbitol and glycine, in particular mannitol, and is aptly present in an injectable formulation according to the present invention at a concentration in the range of 12 to 47 mg/ml.. Saline is not a useful agent in this regard since it may lead to the formation of the hydrochloride salt of lamotrigine which is not very soluble and may result in the formation of a precipitate. The amount of the agent included in the aqueous solution will vary from agent to agent. In the case of mannitol, the amount is preferably from 370 to 470 mg per vial, prior to lyophilisation. Mannitol is particularly useful in that it also has good cake-forming properties.

The reconstituted solution normally has a pH of from 2.5 to 5, preferably 3.4 to 4. The use of such an acidic injectable solution of lamotrigine does not present any significant adverse physiological effect on administration to the patient. It would seem that the pH of the solution is raised to neutral almost as soon as contact is made with the bloodstream, the lamotrigine being rapidly distributed within the bloodstream. It is preferred that this process is not impeded in any way and that therefore neither the freeze-dried formulation nor the injectable solution contains a buffering agent, at least not a strong buffering agent.

The amount of lamotrigine in each vial may vary from 250 to 1000 mg calculated as the base.

Generally from 5 to 10 mg per kg bodyweight of lamotrigine mesylate is intravenously administered per kg bodyweight to patients to provide a therapeutically effective dose for the treatment of SE. The rate of administration of the reconstituted solution providing the required dose may vary.

The present invention further provides a method of treating a patient with epilepsy, which method comprises intravenously administering to the patient an injectable formulation containing lamotrigine substantially as hereinbefore described.

The following examples are provided to assist in the practise of and further illustrate the present invention, and should not however be used to limit the scope of the invention.

1. Mannitol is dissolved in appropriate amount of water. The amount of mannitol needed is calculated to provide tonicity upon reconstitution and may range from 377.85 to 465.5 mg per vial.

2. The mesylate salt of lamotrigine is formed in situ during the manufacturing process described in European patent 21121 and U.S. Pat. No. 4,486,354 by addition of commercially available methanesulfonic acid. Preferably the molar ratio of 3,5-diamino-6-(2,3-dichlorophenyl)-1,2,4-triazine to the acid is approximately 1:1 or higher.

3. When the appropriate amounts of lamotrigine and methanesulfonic acid are combined, the resulting solution pH ranges from approximately 2.8 to 3.5.

4. The solution pH may be adjusted to a range 3.3–3.5 with sodium hydroxide solution or methanesulfonic acid solution.

5. The final concentration of the lamotrigine calculated as free base in solution prior to freeze drying may vary from 1–50 mg per mL, preferably 25 mg per mL.

6. The solution is chemically and physically stable at room temperature for a period of at least 7 days and may be held in suitable stainless steel/glass manufacturing tank for this period of time, if needed.

7. The solution is then sterile filtered and filled in appropriate vials preferably to a fill volume of 10 g.

8. The vials are then loaded into a freeze drier which is precooled to 5° C. prior to loading.

9. The solution is then frozen to −24° C. for 4–5 hours. Primary drying is initiated by ramping the shelf temperature to 0° C. while maintaining the vacuum at 0.5 Torr. After the product temperature reaches the shelf temperature, secondary drying is initiated and conducted at a product temperature of 35° C. for 6–8 hours. The chamber pressure is maintained at 0.5 Torr during lyophilisation.

10. The stability profile of the lyophilized formulation was assessed under stressed and room temperature storage conditions. The resulting data are set forth in Table 2 from which it is evident that the formulation demonstrates physico-chemical stability on storage for 6 months under stressed conditions (40° C./75% RH). No loss in potency and no significant decomposition was observed under these conditions.

11. Reconstitution of the lyophilized formulation with 12.5 mL of sterile water for injection provides an isotonic solution containing 20 mg lamotrigine free base per mL.

12. The stability of the reconstituted product was also assessed. The resulting data are set forth in Tables 3 and 4 from which it is evident that the reconstituted solution is physically and chemically stable when stored at room temperature for a period of at least 3 days.

13. The reconstituted solution can be delivered as is or can be further diluted to 1 to 15 mg lamotrigine per mL. The diluted solution (i.e. 5% dextrose) is chemically and physically stable up to 48 hours at 5 and 25° C. Antimicrobial effectiveness of the product diluted with 5% dextrose is demonstrated for 24 and 48 hours on storage at 25 and 5° C., respectively.

In the above protocol, examples of specific values of lamotrigine, mannitol and methanesulphonic acid that have been employed are as follows.

| Ingredient | Amount per vial (mg) |
|---|---|
| lamotrigine | 250.0 |
| mannitol | 377.8 |
| methanesulphonic acid | 93.75. |

Further methanesulphonic acid, sodium hydroxide and water were added to achieve the required pH and volumes as given in the above protocol.

TABLE 2

Stability of Lyophilized Formulation containing 250 mg Lamotrigine per vial.

| Test Specifications | Appearance a | pH Report Results | Assay lamotrigine 90.0 to 110.0% l.s. | Related Substances g ≦0.5% w/w | Related Substances individual other ≦0.5% w/w | Related Substances Total ≦1.0% w/w | Moisture Content Report Results |
|---|---|---|---|---|---|---|---|
| Initial | b,e | 3.6 | 101.7 | <0.1 | <0.1 | <0.1 | 0.5 |
| | b,f | 3.6 | 101.1 | <0.1 | <0.1 | <0.1 | 0.4 |
| | b,g | 3.6 | 101.1 | <0.1 | <0.1 | <0.1 | 0.4 |
| At Storage Reconstitution Study | b | 3.5 | | | | | |
| 1 day | NC | 3.5 | 102.4 | <0.1 | <0.1 | <0.1 | — |
| 3 day | NC | 3.4 | 103.2 | <0.1 | <0.1 | <0.1 | — |

TABLE 2-continued

Stability of Lyophilized Formulation containing 250 mg Lamotrigine per vial.

| Test Specifications | Appearance a | pH Report Results | Assay lamotrigine 90.0 to 110.0% l.s. | Related Substances g ≦0.5% w/w | individual other ≦0.5% w/w | Total ≦1.0% w/w | Moisture Content Report Results |
|---|---|---|---|---|---|---|---|
| 25° C./60% RH | | | | | | | |
| 1 month | NC | 3.5 | 102.5 | <0.1 | <0.1 | <0.1 | — |
| 3 months | c | 3.6 | 102.8 | <0.1 | <0.1 | <0.1 | — |
| | b,d | 3.4 | 102.8 | <0.1 | — | — | — |
| | b,d | 3.4 | — | — | — | — | — |
| | b,d | 3.4 | — | — | — | — | — |
| 6 months | NC | 3.5 | 100.4 | <0.1 | <0.1 | <0.1 | 0.5 |
| 40° C./75% RH | | | | | | | |
| 1 month | NC | 3.6 | 104.5 | <0.1 | <0.1 | <0.1 | 0.5 |
| 3 months | NC | 3.4 | 103.2 | <0.1 | <0.1 | <0.1 | 0.7 |
| 6 months | NC | 3.5 | 102.6 | <0.1 | <0.1 | <0.1 | 0.6 |
| 30° C./60% RH | | | | | | | |
| 6 months | NC | 3.4 | 102.8 | <0.1 | <0.1 | <0.1 | 0.5 |

[a]A white to off-white freeze-dried powder; reconstituted: A clear colorless solution, with no particulate matter, swirl, or odor.
[b]A white to off-white freeze-dried powder; Reconstituted: clear colorless solution, no particulate matter, no swirl, no odor.
[c]Drug product once reconstituted was white, product had precipitated out, was moderately hazy and cloudy.
[d]Triplicate resample performed to verify the original data value for this test period.
[e]For all data on this line, testing was performed on sampled material from the beginning of the manufacturing run.
[f]For all data on this line, testing was performed on sampled material from the middle of the manufacturing run.
[g]3-Amino-5-keto-6-(2,3-dichlorophenyl)-1,2,4-triazine.

TABLE 3

Chemical Assay of Reconstituted Solution containing 20 mg Lamotrigine per mL

| Storage Conditions | Lamotrigine (percent label strength) | b (percent) |
|---|---|---|
| Specifications | 90–110 | 0–0.5 |
| Initial (reconstituted) | 101.3 | <0.1 |
| 1 day, 30° C.[a] | 99.5 | <0.1 |
| 3 days, 30° C.[a] | 100.1 | <0.2 |

[a]Mean of three samples. Assay by High Performance Liquid Chromatography (HPLC) according to the Analytical Standard.
[b]3-Amino-5-keto-6-(2,3-dichlorophenyl)-1,2,4-triazine.

TABLE 4

Particulate Analysis of Reconstituted Solution containing 20 mg Lamotrigine per mL

| Storage Conditions Specifications | HIAC Royco Analysis-Particles per Container >5 μm 0–100,000 | >10 μm 0–10,000 | >25 μm 0–1,000 |
|---|---|---|---|
| Initial[b] | 593 | 142 | 5 |
| 1 day | 673 | 163 | 3 |
| 3 day | 305 | 28 | 0 |

[a]Mean of five samples.
[b]Average of three separate determinations of five samples.

We claim:

1. A lyophilized formulation of lamotrigine having been prepared by lyophilizing a substantially frozen sterile solution of lamotrigine mesylate and at least one bulking agent in which the pH of said solution is from 2.5 to 4.

2. A lyophilized formulation of lamotrigine having been prepared by lyophilizing a substantially frozen sterile solution of lamotrigine mesylate and at least one bulking agent in which the pH of said solution is from 2.8 to 3.5.

3. A lyophilized formulation of lamotrigine having been prepared by lyophilizing a substantially frozen sterile solution of lamotrigine mesylate and at least one bulking agent in which the pH of said solution is from 3.3 to 3.5.

4. A formulation according to claim 1, wherein the concentration of lamotrigine mesylate prior to lyophilization, calculated as the free base, is from 1 to 60 mg/ml.

5. A formulation according to claim 2, wherein the concentration of lamotrigine mesylate prior to lyophilization, calculated as the free base, is from 1 to 60 mg/ml.

6. A formulation according to claim 3, wherein the concentration of lamotrigine mesylate prior to lyophilization, calculated as the free base, is from 1 to 60 mg/ml.

7. A formulation according to claim 1, wherein the concentration of lamotrigine mesylate prior to lyophilization, calculated as the free base, is from 20 to 30 mg/ml.

8. A formulation according to claim 2, wherein the concentration of lamotrigine mesylate prior to lyophilisation, calculated as the free base, is from 20 to 30 mg/ml.

9. A formulation according to claim 3, wherein the concentration of lamotrigine mesylate prior to lyophilization, calculated as the free base, is from 20 to 30 mg/ml.

10. A formulation according to claim 2, wherein the solution is wholly or substantially aqueous.

11. A lyophilized formulation of lamotrigine having been prepared by lyophilizing a substantially frozen sterile solution of lamotrigine mesylate and at least one bulking agent selected from the group consisting of mannitol, dextrose, lactose, sucrose, sorbitol and glycine in which the pH of said solution is from 2.5 to 4.

12. A formulation according to claim 11, wherein the pH of said solution is from 2.8 to 3.5.

13. A formulation according to claim 11, wherein the concentration of lamotrigine mesylate prior to lyophilization, calculated as the free base, is from 20 to 30 mg/ml.

14. A formulation according to claim 11, wherein the bulking agent is present in an amount of about 192 to 470 mg.

15. A formulation according to claim 11, wherein the bulking agent is mannitol.

16. A formulation according to claim 1, wherein lamotrigine mesylate is formed from lamotrigine free base and methanesulphonic acid, the free base and acid being present in a substantially equimolar ratio.

17. An injectable formulation containing lamotrigine mesylate, reconstituted from a lyophilized formulation of claim 1 using a sterile carrier suitable for intravenous administration, wherein the concentration of lamotrigine mesylate is in the range of 1 to 60 mg/ml, calculated as the free base.

18. An injectable formulation containing lamotrigine mesylate, reconstituted from a lyophilized formulation of claim 1 using a sterile carrier suitable for intravenous administration, wherein the concentration of lamotrigine mesylate is in the range of 1 to 20 mg/ml calculated as the free base.

19. An injectable formulation containing lamotrigine mesylate, reconstituted from a lyophilized formulation of claim 1 using a sterile carrier suitable for intravenous administration, wherein the concentration of lamotrigine mesylate is in the range of 1 to 20 mg/ml, calculated as the free base and wherein the pH of said reconstituted injectable formulation is 3.4 to 4.

20. An injectable formulation containing lamotrigine mesylate, reconstituted from a lyophilized formulation of claim 1 using a sterile carrier suitable for intravenous administration, wherein the concentration of lamotrigine mesylate is in the range of 1 to 60 mg/ml, calculated as the free base, and wherein said sterile carrier suitable for intravenous administration is sterile water for injection or 5% dextrose solution.

21. An injectable formulation containing lamotrigine mesylate, reconstituted from a lyophilized formulation of claim 11 using a sterile carrier suitable for intravenous administration, wherein the concentration of lamotrigine mesylate is in the range of 1 to 20 mg/ml, calculated as the free base and wherein the pH of said reconstituted injectable formulation is 3.4 to 4.

22. An injectable formulation containing lamotrigine mesylate, reconstituted from a lyophilized formulation of claim 11 using a sterile carrier suitable for intravenous administration, wherein the concentration of lamotrigine mesylate is in the range of 1 to 20 mg/ml, calculated as the free base wherein the pH of said reconstituted injectable formulation is 3.4 to 4 and wherein the concentration of said bulking agent is 12 to 47 mg/ml.

23. A method of treating a patient with epilepsy, which method comprises intravenously administering to the patient an injectable formulation according to claim 11.

24. A process for preparing a lyophilized formulation of lamotrigine, which process comprises lyophilizing a substantially frozen sterile aqueous solution of lamotrigine mesylate and at least one bulking agent in which the pH of said solution is from 2.5 to 4.

25. A process for preparing a lyophilized formulation of lamotrigine, which process comprises lyophilizing a substantially frozen sterile aqueous solution of lamotrigine mesylate and at least one bulking agent in which the pH of said solution is from 2.8 to 3.5.

26. A process for preparing a lyophilized formulation of lamotrigine according to claim 25, wherein at least one bulking agent selected from the group consisting of mannitol, dextrose, lactose, sucrose, sorbitol and glycine is included in the aqueous solution prior to lyophilization.

27. A process for preparing a lyophilized formulation of lamotrigine according to claim 25, wherein the bulking agent, mannitol is included in the aqueous solution prior to lyophilization.

* * * * *